US006230087B1

(12) United States Patent
Didomenico et al.

(10) Patent No.: US 6,230,087 B1
(45) Date of Patent: May 8, 2001

(54) VEHICULAR RUNNING LOSS DETECTING SYSTEM

(75) Inventors: John Didomenico; Craig S. Rendahl, both of Tucson, AZ (US)

(73) Assignee: Envirotest Systems Corporation, East Granby, CT (US)

( * ) Notice: Subject to any disclaimer, the term of this patent is extended or adjusted under 35 U.S.C. 154(b) by 0 days.

(21) Appl. No.: 09/502,223

(22) Filed: Feb. 11, 2000

Related U.S. Application Data

(63) Continuation of application No. 09/353,595, filed on Jul. 15, 1999, now abandoned
(60) Provisional application No. 60/092,962, filed on Jul. 15, 1998.

(51) Int. Cl.[7] ............................... G01N 21/25; G01J 1/00
(52) U.S. Cl. .................. 701/29; 701/35; 702/24
(58) Field of Search ................... 701/29, 33, 35; 250/338.5, 339.01, 347, 348; 702/23, 24

(56) References Cited

U.S. PATENT DOCUMENTS

| | | | |
|---|---|---|---|
| 2,930,893 | 3/1960 | Carpenter et al. | 250/43.5 |
| 3,143,648 | 8/1964 | Bradley et al. | 250/43.5 |
| 3,171,027 | 2/1965 | Wallack | 250/83.3 |
| 3,517,190 | 6/1970 | Astheimer | 250/43.5 |
| 3,593,023 | 7/1971 | Dodson et al. | 250/430 |
| 3,630,072 | 12/1971 | Traver | 73/23.31 |
| 3,696,247 | 10/1972 | McIntosh et al. | 250/339.07 |
| 3,761,715 | 9/1973 | Menzies | 250/338.5 |
| 3,761,724 | 9/1973 | Dennis | 250/565 |
| 3,766,380 | 10/1973 | Menzies | 250/343 |
| 3,841,763 | 10/1974 | Lewis | 356/438 |
| 3,849,005 | 11/1974 | Girard et al. | 356/438 |
| 3,891,848 | 6/1975 | Fletcher et al. | 250/345 |
| 3,908,167 | 9/1975 | Hadden et al. | 324/166 |
| 3,931,462 | 1/1976 | Exton | 348/162 |
| 3,957,372 | 5/1976 | Cross et al. | 356/51 |
| 3,958,122 | 5/1976 | Cross et al. | 250/346 |
| 3,976,884 | 8/1976 | Acton et al. | 250/343 |
| 4,135,092 | 1/1979 | Milly | 250/343 |
| 4,160,373 | 7/1979 | Cross et al. | 73/23.31 |
| 4,204,121 | 5/1980 | Milly | 250/343 |
| 4,204,768 | 5/1980 | Nguyen | 356/243.1 |
| 4,323,777 | 4/1982 | Baskins et al. | 250/339.04 |
| 4,390,785 | 6/1983 | Faulhaber et al. | 250/330 |
| 4,426,640 | 1/1984 | Becconsall et al. | 340/632 |
| 4,489,239 | 12/1984 | Grant et al. | 250/339.03 |

(List continued on next page.)

OTHER PUBLICATIONS

Peterson, J., et al., "Find and Fix the Polluters"; Chemtech, Jan. 1992, pp. 47–53.
Bishop, G., et al., "Analytical Approach—IR Long Oath Photometry: A Remote Sensing Tool for Automotive Emissions," Analytical Chem., V. 61, p. 617A (May 15, 1989).
Chaney, L., "The Remote Measurement of Traffic Generated Carbon Monoxide," Journal of Air Pollution Control Assoc., V. 33, No. 3, Mar. 1983, p. 220–222.
Stevens, R., et al.,"DOAS Urban Pollution Measurements," SPIE vol. 1433, 1991. (Month is not available).
Hosizaki, H., "Final Report Vehicle Inspection Instrumentation", Lockheed Palo Alto Research Laboratory, Jun. 1973.

*Primary Examiner*—Tan Nguyen
(74) *Attorney, Agent, or Firm*—Hunton & Williams

(57) ABSTRACT

A system and method for detecting running loss emissions is provided. A remote sensing device is used to detect vehicular exhaust emissions. The detected emissions are analyzed to determine a characteristic profile. The characteristic profile is processed to determine whether the profile is suspect or invalid. Invalid and suspect profiles are further analyzed to determine if running losses (e.g., leaky gas cap vapors, blow by emissions, etc.) are present. Profiles labeled as containing running losses may be further processed to generate statistical information, deliver notification to vehicle owners, or other actions.

16 Claims, 2 Drawing Sheets

U.S. PATENT DOCUMENTS

| | | | |
|---|---|---|---|
| 4,490,043 | 12/1984 | Cramp | 356/407 |
| 4,490,613 | 12/1984 | Brame | 250/341 |
| 4,492,862 | 1/1985 | Grynberg et al. | 250/255 |
| 4,496,839 | 1/1985 | Berstein et al. | 250/341 |
| 4,516,858 | 5/1985 | Gelbwachs | 356/437 |
| 4,553,032 | 11/1985 | Borken et al. | 250/339.12 |
| 4,707,603 | 11/1987 | Jaatinen et al. | 250/339.08 |
| 4,746,218 | 5/1988 | Lord | 356/437 |
| 4,771,176 | 9/1988 | Krempl et al. | 250/339 |
| 4,795,253 | 1/1989 | Hunt et al. | 356/51 |
| 4,810,884 | 3/1989 | Carlson | 250/338.5 |
| 4,924,095 | 5/1990 | Swanson | 250/338.5 |
| 5,099,437 * | 3/1992 | Weber | 702/187 |
| 5,210,702 | 5/1993 | Bishop et al. | 702/24 |
| 5,246,868 | 9/1993 | Busch et al. | 436/101 |
| 5,252,828 | 10/1993 | Kert et al | 250/339.13 |
| 5,319,199 | 6/1994 | Bishop et al. | 250/338.5 |
| 5,327,356 | 7/1994 | Dall'era et al. | 702/22 |
| 5,343,043 | 8/1994 | Johnson | 250/338.5 |
| 5,371,367 | 12/1994 | DiDomenico et al. | 250/338.5 |
| 5,401,967 | 3/1995 | Bishop et al. | 250/338.5 |
| 5,418,366 | 5/1995 | Jack et al. | 250/338.5 |
| 5,451,787 | 9/1995 | Taylor | 250/338.5 |
| 5,489,777 | 2/1996 | Bishop et al. | 250/338.5 |
| 5,498,872 | 3/1996 | Bishop et al. | 250/338.5 |
| 5,550,737 * | 8/1996 | Tedeschi | 701/31 |
| 5,591,975 | 1/1997 | Jack et al. | 250/338.5 |
| 5,726,450 | 3/1998 | Bahan et al. | 250/338.5 |
| 5,729,452 * | 3/1998 | Smith et al. | 701/29 |

* cited by examiner

VEHICULAR RUNNING LOSS DETECTING SYSTEM

This application is a continuation of application Ser. No. 09/353,595, filed Jul. 15, 1999, now abandoned which claims priority to Provisional Application Ser. No. 60/092,962 filed Jul. 15, 1998.

FIELD OF THE INVENTION

This invention relates to a vehicular running loss detecting system and method to determine emissions (e.g., hydrocarbon emissions) from a vehicle, in addition to emissions from the exhaust system of the vehicle.

BACKGROUND OF THE INVENTION

Environmental pollution is a serious problem that is especially acute in urban areas. Motor vehicles, such as automobiles, are a considerable contributor to this pollution dilemma, especially those not equipped with anti-pollution devices, or with breaches in their structural integrity. Centralized systems to detect vehicle emissions are known, but require vehicles to be taken to the centralized test facilities. Systems for remotely sensing vehicle emissions (e.g., roadside) also are generally known. These remote systems, however, typically detect emissions emanating from the exhaust system of a moving vehicle (e.g., an automobile). However, other types of emissions known as running losses also exist. Running losses are defined by the EPA, and include hydrocarbon emissions from sources such as evaporation from a gas cap, blow-by emissions (e.g., residual plume from other vehicles or losses from an engine compartment or fuel lines that are swept under the car and emerge at the rear of the vehicle) and other running losses. In some cases, one or more running loss plumes mix with an exhaust plume. In some cases, they may cause a system to invalidate the test for that vehicle. Other drawbacks also exist.

SUMMARY OF THE INVENTION

An object of this invention is to overcome theses and other drawbacks in known systems and methods.

Another object of the invention is to provide a system and method for detecting running losses from vehicles.

Another object of the invention is to remotely detect running losses from vehicles.

Another object of the invention is to identify a plume that comprises emissions from two or more sources.

These and other objects of the invention are accomplished by various embodiments of the invention. One embodiment of the present invention provides a vehicular running loss detecting system and method that reliably identifies the existence of running loss. Running loss refers to emissions originating from sources such as evaporative loss (e.g., from a gas cap) and directly from the vehicle's engine (ie., from the pistons), often referred to as, "blow-by". According to one aspect of the invention, this is accomplished by storing emission data from a control vehicle having known running loss. Preferably, at least HC and $CO_2$ emission patterns are collected from the control vehicle with known running losses and stored. In this way, a plurality of characteristic or "signature" emission patterns may be obtained for various types of running losses. These signature emission patterns may then be stored in a database. Emissions from vehicles may be detected and compared to one or more predetermined criteria indicative of the presence of a running loss. Such predetermined criteria may be obtained from the signature emission patterns in the database. One or more characteristics of these signature emission patterns can be employed to identify potential running losses from a vehicle.

According to one embodiment, the emissions detection may be performed by a remote sensing device, such as RSD-1000, RSD-2000, or RSD-3000 manufactured by Environmental Systems Products, Inc., Tucson, Ariz., wherein the process control software is modified to perform the novel functions set forth herein and wherein a database of stored emissions patterns is provided.

These and other features of the invention will be apparent to those skilled in the art from the following detailed description of preferred embodiments, taken together with the accompanying drawings.

DETAILED DESCRIPTION OF THE INVENTION

According to one embodiment of the present invention, a remote emissions sensing system with running loss detection comprises a source/detector module for detecting the composition and concentration of emissions originating from a vehicle's exhaust system and from one or more running loss sources. For example, the remote emissions sensor preferably detects vehicle emissions, such as those from an exhaust plume to determine the concentration of constituents such as HC, CO, $CO_2$, $NO_x$, and other constituents of interest. According to one embodiment of the invention, certain plume criteria are evaluated to determine the existence or potential existence of two or more sources of the emissions. Thus, the system possesses the ability to differentiate between emissions solely from an exhaust plume and emissions which also include components originating from a source other than the vehicle's tailpipe exhaust (e.g., running loss). If the system determines that at least a second source of emissions exists or may exist, the processor may compare one or more characteristics of the detected emission pattern with one or more characteristic of stored signature emission patterns to identify a potential running loss as a source of emissions.

Figure 1:
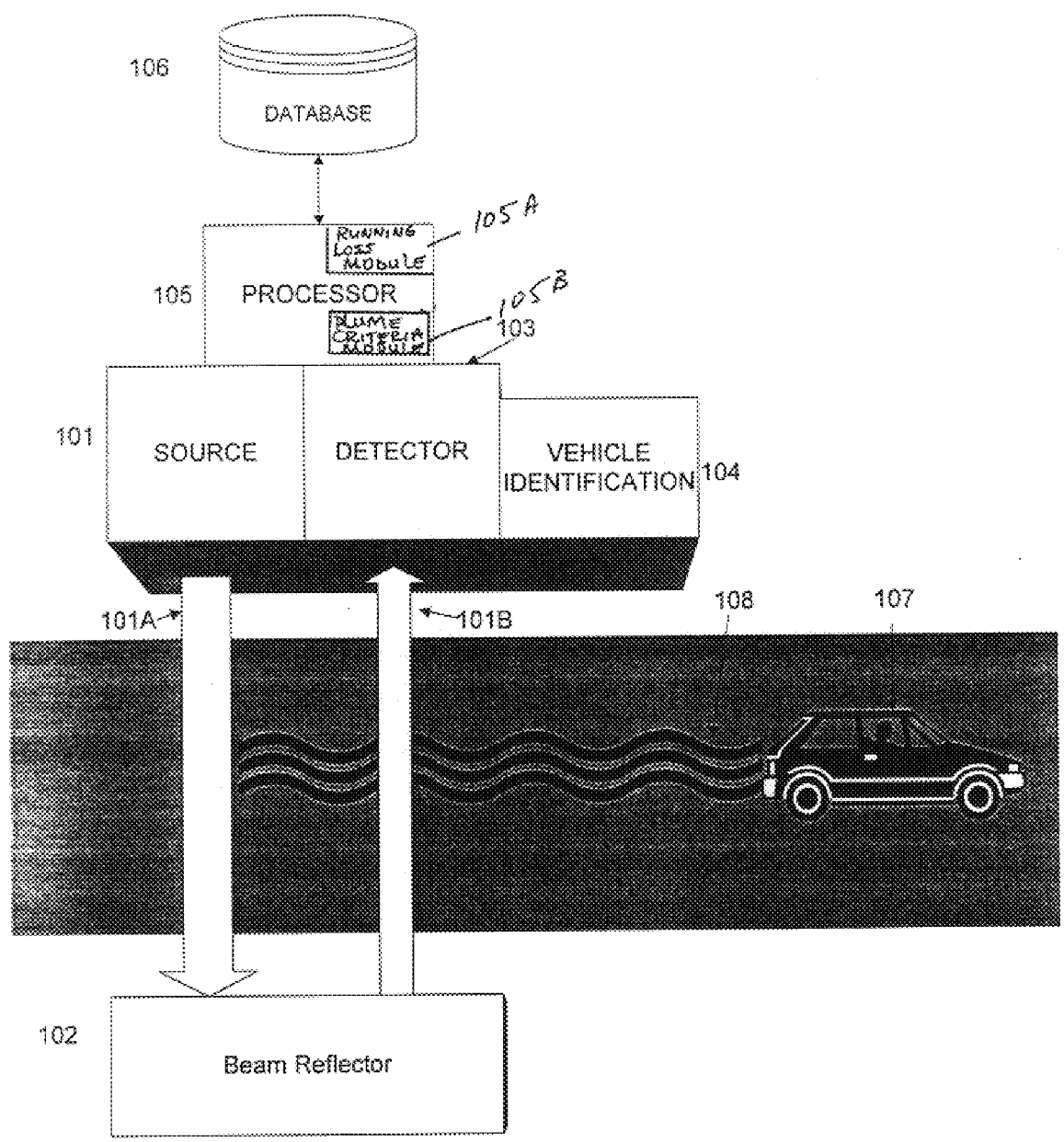
FIG. 1 is a schematic illustration of a remote emissions sensing system with the capability of detecting one or more running losses, according to one embodiment of the invention.

As shown in FIG. 1, a remote emissions detection system may compose a system such as the RSD-1000, RSD-2000 or RSD-3000 or one such as that described in U.S. Pat. No. 5,210,702, which is incorporated herein by reference. For example, the system may comprise a source 101 of electromagnetic radiation, for producing an optical beam 101A, including one or more predetermined wavelengths, such as an infrared and/or ultraviolet beam, and a beam reflector 102 for reflecting a beam 101B to a detector unit 103. A vehicle identification device 104 (such as an imaging device, an automated license plate reader or other identification device) and a processor 105 are also provided. As a vehicle 107 approaches or passes the system, vehicle identification device 104 identifies the vehicle, then captures and interprets the vehicle's license plate number. Capture devices and automatic license plate readers are known to those in the art. The processor 105, in part, performs an analysis of the plume to analyze the exhaust emissions in a known manner. Preferably, the processor 105, according to one aspect of the present invention, includes a running loss module 105A and a plume criteria module 105B.

In operation, the source beam 101A passes through the plume 108 of vehicle 107, to beam reflector 102 and reflected beam 101B is received by detector 103. Changes in attenuation of the source beam represent absorption of the source beam by vehicle emissions, and possibly from running losses. According to one embodiment, multiple samples are taken over a predetermined period. The detector may include a reference detector and detectors for one or more of hydrocarbons (HC), CO, $CO_2$ and $NO_x$, where x is an interger. These samples may be analyzed by processor 105 to determine the HC, CO, $NO_x$, and $CO_2$ absorption levels of these samples. These absorption levels may then be translated into concentration levels for each sample, according to known techniques.

According to one embodiment of the present invention, after a predetermined number of emissions measurements (e.g., 50) are taken over a predetermined period (e.g., 0.5 seconds) (ie., 50 measurements with 10 millisecond intervals), a plume validation process may be performed on those measurements by plume criteria module 105B of processor 105. The plume validation process may include one or more steps or combinations thereof, selected from those identified below and/or other steps.

For example, plume validation may include determining whether there is an absorption of light on the reference channel. If so, the deflection caused by absorption is then subtracted from all of the measurements. If the reference channel deflection exceeds a predetermined amount, all of the impacted measurements may be discarded, or adjusted by the amount of deflection. A pre-vehicle and post-vehicle beam block measurement on the reference channel may be taken to determine a baseline voltage for all of the measurements. That baseline voltage may then be subtracted from the measurements on one, some or all of the other channels as well. To validly determine the concentration(s) of various emission elements, a minimum amount of $CO_2$ may be required, since each (or some) values are determined by use of a ratio to the $CO_2$ concentration in a known manner. Measurements from a time interval for which the $CO_2$ concentration not at least about 0.1% absolute, for example, may be discarded. After these adjustments are made to the measurements, a best fit (or other) curve plotting algorithm may be applied to plot these measurements on a graph with the X coordinate being the $CO_2$ measurement and the Y coordinate being the measurement for another emission of interest, such as CO, HC or $NO_x$, for example.

Another step in the plume validation may include performing a statistical analysis to determine statistical outliners. According to one embodiment, if an individual measurement for the emission being plotted (on the Y-axis) is more than a predetermined amount or percentage away from the best fit line (or other curve), that measurement may be discarded. For example, if the Y-axis value of a measured data point is more than 10% above (or below) a best fit line, that measurement may be discarded. Additionally or alternatively, a measurement may be discarded if it is greater than a predetermined maximum value. For example, the maximum value may be established as the lesser of 10% or the ratio of the maximum digitizer noise to the largest measurement in the group, or some other value.

To sufficiently establish a slope (target emission/$CO_2$) from a plume, it is generally desirable to have a predetermined number of measurements over a predetermined interval of time. Overall plume strength can be determined by observing the amount of $CO_2$ in an exhaust plume. This measure of strength is possible because $CO_2$ is the most plentiful of all exhaust gases. If a plume deteriorates in less than a desired amount of time, for example, that plume may be invalid. To make this determination, the total number of measurements may be divided into two or more duty cycles of half (or some other fraction) of the predetermined interval (e.g., for a half second interval two duty cycles of one quarter second each). The $CO_2$ measurements in the second duty cycle may then be monitored to determine whether there are a sufficient number of measurements above a predetermined level in that cycle for a sufficient plume.

Another plume validation criteria may be determining if there is too much noise. Noise may be determined by analyzing the number of measurements that are a predetermined amount away from the best fit line (standard error). A significant amount of variation from the best fit line is a sign that the plume is too noisy and should be noted as such.

If the measurements pass these criteria, the individual readings are considered to determine whether the readings are consistent with expectations. If the readings exceed reasonable levels, the measurements may be invalidated. For example, if the measurements exceed 21% for CO, 16% for $CO_2$, 20,000 PPM for HC, 7,000 PPM for $NO_x$, or 21% for both CO and $CO_2$, the plume may be invalidated, or at a minimum, be noted as suspect. The same is true if a plume analysis yields negative values, or if a plume yields an inordinately low $CO_2$, concentration (e.g., 6.0%).

According to one aspect of the invention, rather than simply invalidating or marking such a plume as suspect, a further step may be performed. That step involves determining if at least a second source of the emission may be present. The existence of a second source (if not identified as such) may cause an existing system to invalidate or flag as suspect a particular plume. According to this aspect of the present invention, the existence of a second source of emission (e.g., from running losses) may be determined.

Figure 2:
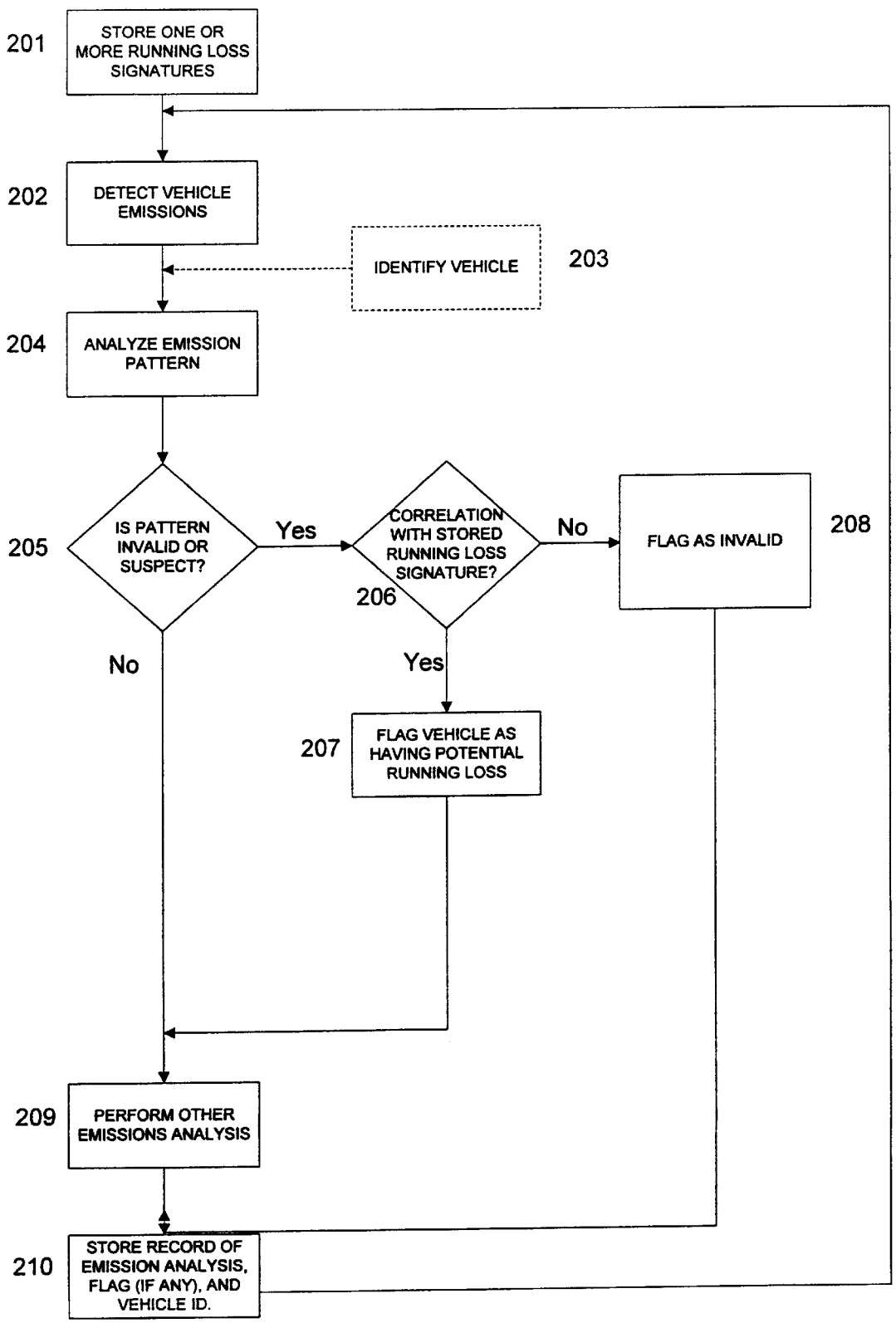
FIG. 2 is a flow chart illustrating the operation of the running loss detection system of FIG. 1 according to one embodiment of the invention.

According to one embodiment, as illustrated in FIG. 2, the processor may perform one or more functions to identify the existence of a second source of emission (e.g., from running loss).

According to one embodiment, emission pattern signatures may be obtained and stored (step 201) in database 106 associated with processor 105. This may be done by having a control vehicle release known quantities of emissions representing one or more standard types of running losses (e.g., from a canister attached to a predetermined location of a control vehicle). For example, a test vehicle may be equipped with an HC releasing apparatus, such as a cylinder, at locations commonly known or likely to emit running loss. The rates of gaseous emission and other criteria may also be varied for each location in the vehicle where the HC releasing apparatus is installed. As the control vehicle passes through the running loss detection system, the emission patterns may be stored in database 106 as emission pattern signatures (step 201). The emission patterns which are analyzed for running loss emissions generally comprise certain concentration levels of HC (and $CO_2$), since running losses are typically comprised of these components. Such signature emissions patterns may define emissions patterns for a vehicle with a running loss from a particular location in the vehicle emitting at a specific release rate. Other criteria such as vehicle speeds, wind directions, etc. may be accounted for as well.

When a vehicle 107 with unknown emissions goes through the remote emissions detection system, its emissions are detected (step 202). At some convenient time, the vehicle may be identified (step 203). The processor 105 analyzes the emissions detected (step 204). This may include determining the concentrations of one or more of HC, CO, $NO_x$, and $CO_2$ (or other constituents) by analysis of the detected emissions patterns (step 204). If, based on predetermined plume criteria (module 105B), the processor determines that the test data is invalid or suspect (step 205), the test data is not simply discarded, nor is the test simply invalidated or tagged as suspect, as may be done in prior systems. Rather, if the pattern is determined at step 205 to be suspect or invalid, the processor 105 determines if there is potentially at least a second source of emissions, in addition to the tailpipe exhaust plume. For example, the processor may invoke running loss module (105A) to determine if a detected emissions pattern or portion thereof correlates with a stored running loss (step 206). If yes, the vehicle is flagged as having potential running loss (step 207) and control passes to step 209. If no (at step 206), the data may be flagged as invalid (step 208) and control passes to step 209. If the pattern is not determined to be invalid or suspect at step 205, control passes to step 209. At step 209, emissions analysis is performed (e.g., standard exhaust emission analysis). At step 210, the processor stores a record of the emission analysis, flag (if any) and vehicle identification information. Preferably, if a second source of emissions is suspected to exist, the detected (and $CO_2$) levels for the vehicle are analyzed and compared to one or more characteristics of the signature emission patterns stored in the computer's database. For running losses, if the $HC/CO_2$ levels match or correlate to a certain degree with the emission pattern signatures in the database, running loss is considered likely to exist Some embodiments of the system may compensate for running loss, under appropriate circumstances, by adjusting the emission analysis to remove the portion of the signal which is due to running loss. While not shown in FIG. 2, further analysis may be performed to identify the type, source, composition and/or concentration of running loss. Other tests may be performed in that case. In addition, the system may compile data regarding those vehicles flagged as having running losses. For example, statistics pertaining to the make, model, year, and other characteristics of vehicles exhibiting running loss emissions may be compiled. Other types of data may also be compiled.

In some embodiments of the invention the measurements not effected by the presence of running losses may be retained, or processed in other ways. For example, running losses which may contain primarily HC emissions, may not affect tailpipe emission measurements of CO or $No_x$. Therefore, the CO or $NO_x$, measurements may be subject to further processing and analysis.

In some embodiments of the invention the identification of a vehicle having running losses may be used to enforce various emission standards. For example, a vehicle having "acceptable" tailpipe emissions may, in fact, be contributing unacceptable levels of pollution through running losses. The present system identifies vehicles with running losses, and may be used by appropriate authorities to require repairs, inspection, or other corrective procedures.

Other embodiments and uses of the invention will be apparent to those skilled in the art from consideration of the specification and practice of the invention disclosed herein. The specification and examples should be considered exemplary only. The scope of the invention is only limited by the claims appended hereto.

What is claimed is:

1. A method for analyzing exhaust emissions, the method comprising the steps of:

detecting exhaust emissions, using a remote emissions detecting system to capture exhaust emissions data from a moving vehicle, and processing the exhaust emissions data to provide a characteristic profile;

determining whether the characteristic profile is invalid or suspect by comparing the characteristic profile to predetermined values to determine if the characteristic profile exceeds or lags the predetermined values; and determining whether an invalid or suspect characteristic profile correlates to at least one predetermined criterion which indicates the presence of running losses by comparing one or more characteristics of the invalid or suspect characteristic profile to one or more characteristics of a stored emission pattern signature representing running loss.

2. The method of claim 1 further comprising the step of:

flagging the characteristic profile according to the result of the step of determining if there is an indication of the presence of running loss.

3. The method of claim 1 wherein the step of determining whether an invalid or suspect characteristic profile correlates to at least one predetermined criterion which indicates the presence of running losses by comparing the invalid or suspect characteristic profile to the stored emission pattern signature further comprises:

accessing a database of one or more stored emission pattern signatures representing running loss.

4. The method of claim 2 further comprising the step of:

using the flagged characteristic profile indicating the presence of running loss, to take other action.

5. The method of claim 4 wherein the step of using the flagged characteristic profile to take other action further comprises:

causing a notification to issue, wherein the notification comprises a request to remedy the running loss.

6. The method of claim 4 wherein the step of using the flagged characteristic profile to take other action further comprises:

compiling data regarding the attributes of vehicles exhibiting running loss.

7. The method of claim 6 wherein the step of compiling data regarding the attributes of vehicles exhibiting running loss further comprises:

compiling data regarding at least one of the make, model, and year of the vehicle.

8. The method of claim 1 further comprising the step of:

removing the portion of characteristic profile indicative of running loss to create a corrected characteristic profile for the vehicle exhaust plume.

9. The method of claim 1 further comprising the steps of:

processing a characteristic profile of a vehicle exhibiting running loss to determine a concentration of at least one exhaust emission constituent selected from the group consisting of: CO, $CO_2$, and $NO_x$, where x is an interger.

10. A system for analyzing exhaust emissions, the system comprising:

a remote detector system to detect exhaust emissions data from a moving vehicle, and process the exhaust emissions data and create a characteristic profile;

a first decision module to determine whether the emission signature profile indicates that the detected exhaust emissions are invalid or suspect by comparing the characteristic profile to predetermined values to determine if the characteristic profile exceeds or lags the predetermined values; and a second decision module to determine whether the any invalid or suspect emission signature profile indicates the presence of running loss by comparing one or more characteristics of the invalid or suspect characteristic profile to one or more characteristics of a stored emission pattern signature representing running loss.

11. The system of claim 10 further comprising:

flagging module to label the emission signature profile according to the result of the determination made by the second decision module.

12. The system of claim 11 further comprising:

a storage repository comprising the stored emission pattern signatures representing running loss.

13. The system of claim 10 further comprising:

a notification module which causes a notification to issue based on the determination of the second decision module, wherein the notification comprises a request to remedy the running loss.

14. An electronic storage medium having code embodied therein for causing a processing system to analyze detected exhaust emissions, the medium comprising:

analyzing code that causes a processor to analyze the detected exhaust emissions to create an emission signature profile;

decision code that causes a processor to determine whether the emission signature profile indicates that the detected emissions are invalid or suspect by comparing the characteristic profile to predetermined values to determine if the characteristic profile exceeds or lags the predetermined values; and correlation code that causes a processor to determine whether any invalid or suspect signature profiles correlate to a predetermined criteria indicative of the presence of running loss by comparing one or more characteristics of the invalid or suspect characteristic profile to one or more characteristics of a stored emission pattern signature representing running loss.

15. An electronic storage medium as claimed in claim 12 further comprising:

flagging code that causes a processor to flag the emission signature profiles according to the result of the determination of the emission signature profile's correlation to a predetermined criteria.

16. An electronic storage medium as claimed in claim 14 further comprising notification code that causes a processor to issue a notification based on the result of the determination of the emission signature profile's correlation to a predetermined criteria.

* * * * *